(12) United States Patent
Hiltawsky

(10) Patent No.: US 7,740,587 B2
(45) Date of Patent: Jun. 22, 2010

(54) FLYWHEEL VIBRATOR

(75) Inventor: Karsten Hiltawsky, Schwerte (DE)

(73) Assignee: General Electric Company, Niskayuna, NY (US)

(*) Notice: Subject to any disclaimer, the term of this patent is extended or adjusted under 35 U.S.C. 154(b) by 890 days.

(21) Appl. No.: 11/163,912

(22) Filed: Nov. 3, 2005

(65) Prior Publication Data

US 2007/0100240 A1   May 3, 2007

(51) Int. Cl.
*A61B 8/14* (2006.01)
(52) U.S. Cl. .................. 600/459; 600/437; 600/438; 600/439; 601/2
(58) Field of Classification Search .......... 600/425, 600/431, 437, 459, 587; 601/1, 2, 3
See application file for complete search history.

(56) References Cited

U.S. PATENT DOCUMENTS

| | | | | |
|---|---|---|---|---|
| 3,581,593 A | * | 6/1971 | Robinson | 74/443 |
| 5,181,514 A | * | 1/1993 | Solomon et al. | 600/444 |
| 5,307,816 A | * | 5/1994 | Hashimoto et al. | 600/439 |
| 5,445,154 A | * | 8/1995 | Larson et al. | 600/459 |
| 5,562,096 A | * | 10/1996 | Hossack et al. | 600/446 |
| 2005/0107700 A1 | | 5/2005 | Morris et al. | |

FOREIGN PATENT DOCUMENTS

DE   199 36 554 C2   8/2001

\* cited by examiner

*Primary Examiner*—Long V Le
*Assistant Examiner*—Nigel Fontenot
(74) *Attorney, Agent, or Firm*—Joseph J. Christian

(57) ABSTRACT

The present invention is directed to an imaging tool to introduce a vibrational force into an object. The imaging tool includes a pair of flywheels that are driven by a motor in opposing rotational paths so as to introduce a harmonic mechanical excitation to the object. The imaging tool is constructed to be of handheld size so as to be suitable for ultrasound and is RF-compatible with MR scanners.

7 Claims, 3 Drawing Sheets

FLYWHEEL VIBRATOR

BACKGROUND OF THE INVENTION

The present invention relates generally to diagnostic imaging and, more particularly, to an imaging tool that induces harmonic excitation within an object. Accordingly, the present invention is particularly applicable to elastography.

Increasingly, there has been a desire to image the elastic properties of tissue either through ultrasound or magnetic resonance imaging or other imaging techniques. Specifically, elastography has been identified as an effective tool in identifying malignant tumors within an object. That is, it is well known that malignant tumors are stiffer relative to their surrounding tissue when such tumors reach a requisite size. As such, by gathering information about the elastic properties of tissue, either through elastic field parameters, e.g., mechanical strain, or from elastic material parameters, e.g., Young's modulus, malignant tumors may be readily identified.

To perform such an elastography, it is necessary to apply a mechanical force to the object under investigation and measure the resulting mechanical displacement or strain field, from which other parameters may be determined. As referenced above, the observation of displacement is typically carried out either by ultrasound or another imaging technique, such as magnetic resonance (MR) imaging.

The drawback of current techniques of elastography lies in the poor signal-to-noise ratio of the displacement measurements, especially in case of freehand approaches. Accordingly, it is desirable to apply a harmonic mechanical excitation to the object, so that the resulting displacements will have a harmonic character. However, it is desirable for such a solution to fall within other desirable constraints; namely, excitation to an object in the range of 1-600 Hz as well as incorporation in a handheld tool for ultrasound or a tool that is RF-compatible for MR imaging.

BRIEF DESCRIPTION OF THE INVENTION

The present invention is directed to an imaging tool to introduce a vibrational force into an object that overcomes the aforementioned drawbacks. The imaging tool includes at least one pair of flywheels that are driven by a motor in opposing rotational paths so as to introduce a harmonic mechanical excitation to an object. The imaging tool is constructed to be of handheld size so as to be suitable for ultrasound and is RF-compatible with MR scanners. Particularly, in the context of ultrasound, it is contemplated that the imaging tool may be mounted to or integrated within the ultrasound transducer probe.

Therefore, in accordance with one aspect of the present invention, an imaging tool to introduce a vibrational force into an object is disclosed. The imaging tool includes a housing and at least a pair of flywheels disposed in the housing. The imaging tool further has a motor disposed in the housing and operably connected to the pair of flywheels to cause rotation of the flywheels to introduce a harmonic mechanical excitation to an object placed in proximity to the housing.

In accordance with another aspect of the invention, an ultrasound transducer probe is presented and includes a probe housing as well as an array of piezoelectric transducer elements disposed within the housing that when energized cause transmission of ultrasonic sound waves to an object to be imaged. The transducer elements are also constructed to be impinged by ultrasonic sound waves and in response thereto emit electrical current that can be processed to reconstruct an image of the object. The transducer probe further includes a mechanical vibrator that causes harmonic excitation of tissue within the object during imaging of the object.

According to another aspect, the present invention is directed to an ultrasound system having a CPU that coordinates data collection and image reconstruction for an ultrasound scan. The system further has a display connected to the CPU that displays an image reconstructed from acquired ultrasound data processed by the CPU. A transducer probe is connected to the CPU and sends and receives sound waves for the acquisition of ultrasound data. The ultrasound system further has a vibrator connected to the CPU that causes harmonic excitation within an object to be imaged in the ultrasound scan.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The present invention is directed to an imaging tool for inducing harmonic excitations in an object to be scanned. The imaging tool is particularly applicable to elastography carried out either with an ultrasound system or an MR system. While the present invention is applicable with ultrasound, MR, or other imaging systems, for purposes of illustration, the present invention will be described with respect to an ultrasound imaging system.

Figure 1:
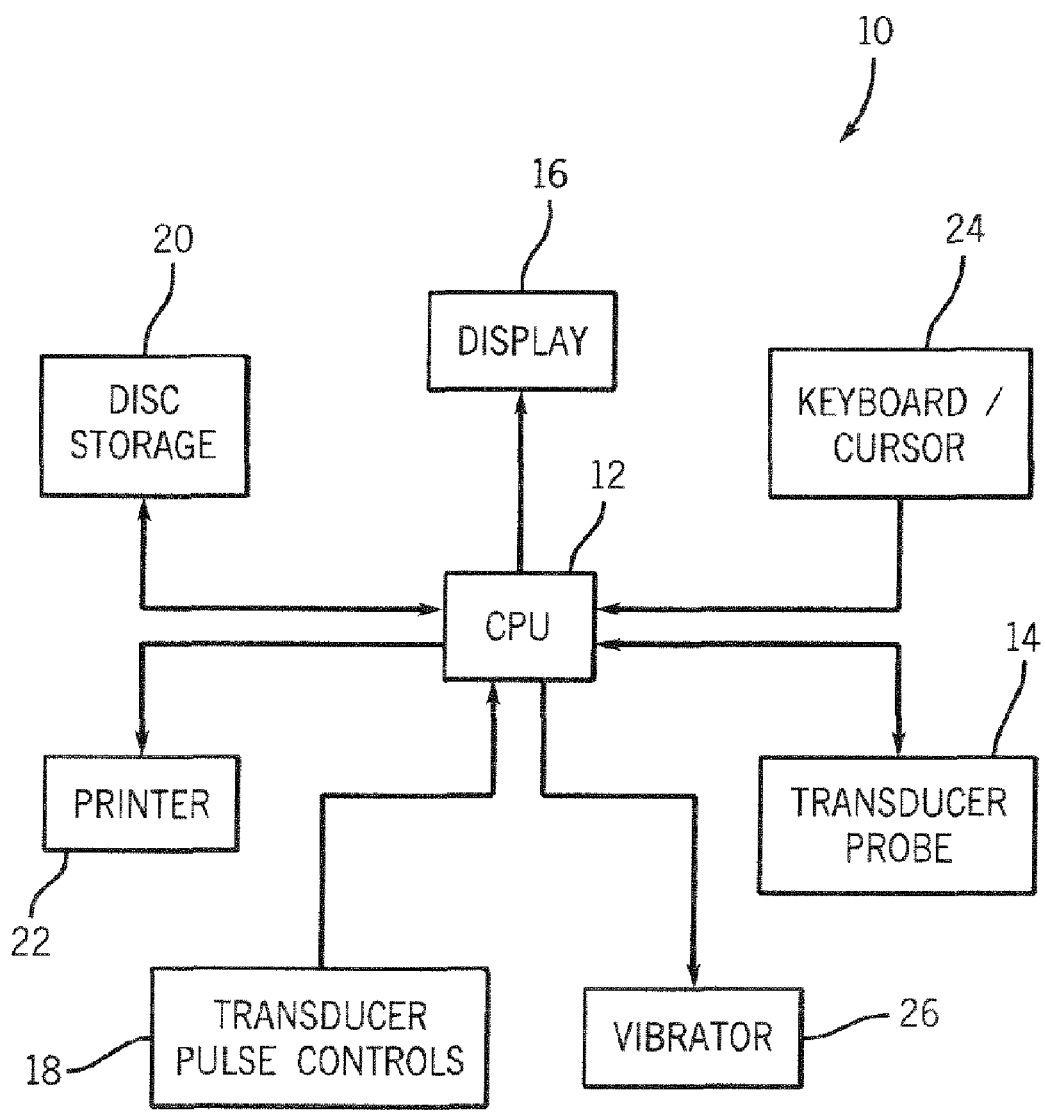
FIG. 1 is a schematic representation of an ultrasound system according to one aspect of the present invention.

FIG. 1 illustrates schematically an ultrasound imaging system 10 according to the present invention. The ultrasound system or machine 10 includes a central processing unit (CPU) 12 that is operationally connected to a transducer probe 14 that generates and receives ultrasonic sound waves. In accordance with conventional construction, the transducer probe generates and receives sound waves using piezoelectric crystals that, when energized by an electric current, change shape rapidly so as to produce sound waves that travel outwardly to an object to be imaged. Conversely, when sound or pressure waves hit the piezoelectric crystals, the crystals emit electrical currents that can be processed by the CPU and reconstructed to form an image that is displayed on computer monitor or display 16. Ultrasound system 10 further includes transducer pulse controls 18 that allow the operator, the sonographer, to set and change the frequency and duration of the ultrasound pulses as well as the scan mode of the ultrasound machine. The commands from the operator are translated into changing electric currents that are applied to the transducer piezoelectric elements.

CPU 12 includes a microprocessor, memory, amplifiers, and power supplies for the microprocessor and transducer probe 14. The CPU sends electrical currents to the transducer probe to emit sound waves and also receives the electrical pulses from the probes that were created from the returning echoes. The CPU also performs the necessary calculations involved in the processing of the received data for image reconstruction as well as other measurements that are carried out. Once the raw data is processed, the CPU forms the image on monitor 16. The CPU may also store the processed data and/or image on a disc 20 or cause a copy of the image to be printed on printer 22. CPU 12 also communicates with a keyboard/cursor which operates as an input device to allow the operator to add notes and to take measurements from the data. As will be described in greater detail below, ultrasound system 10 further includes a vibrator 26 that will be used to induce a harmonic mechanical excitation in the object to be imaged. This harmonic excitation will be particularly advantageous for elastography and related studies.

Figure 2:
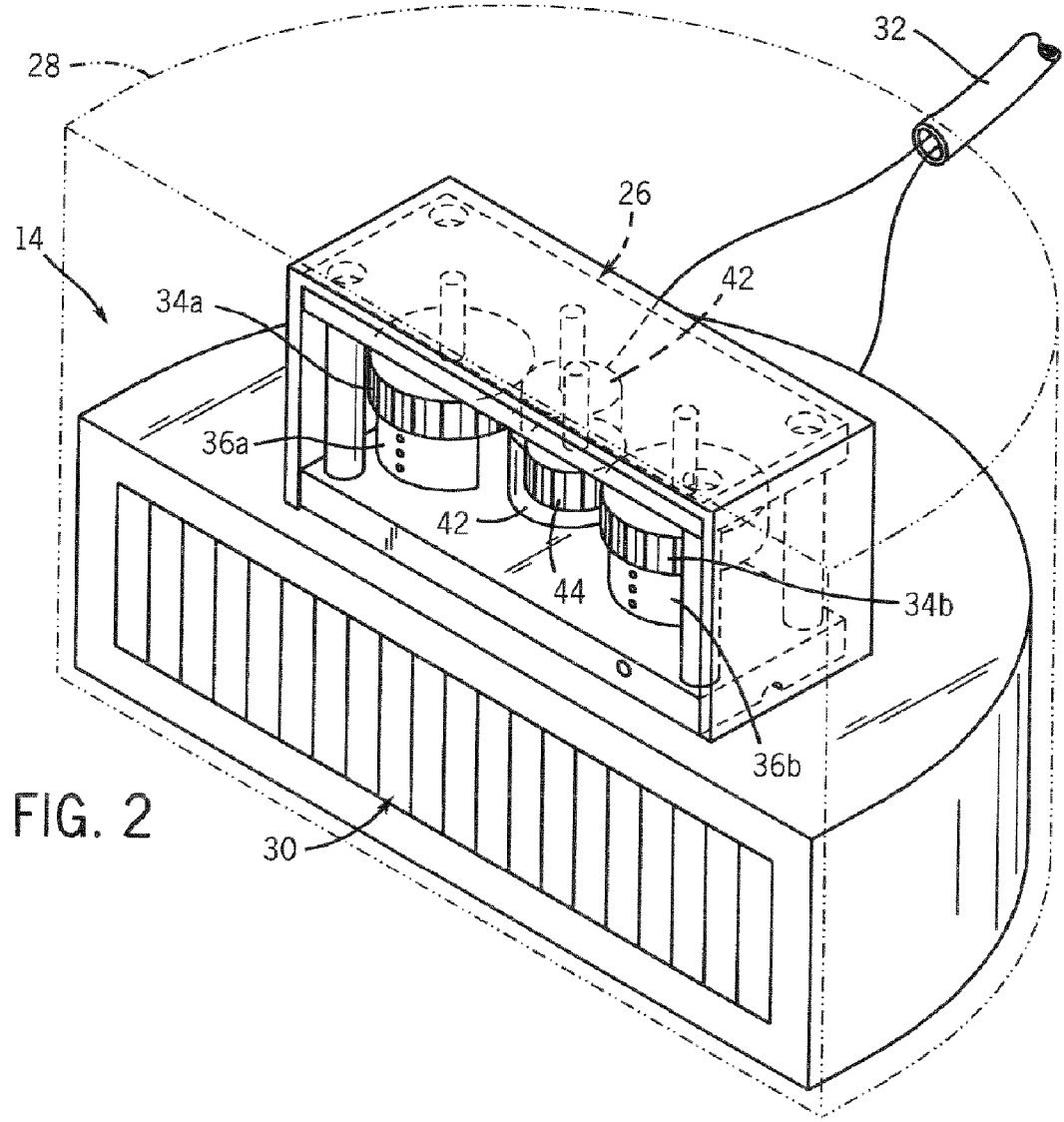
FIG. 2 is a perspective view of an integrated transducer and vibrator according to another aspect of the present invention.

Referring now to FIG. 2, a transducer probe 14 according to one aspect of the present invention is illustrated. In this exemplary embodiment, the transducer probe and the vibrator 26 are enclosed within a common housing 28. As described above, the transducer probe 14 includes an array of piezoelectric elements 30 that transmit sound waves and receive echoes therefrom. The acquired data is communicated to the CPU, FIG. 1, via control cable 32.

As will be described more fully below, the vibrator 26 includes cog wheels 34(a), 34(b) that drives a pair of flywheels 36(a), 36(b) to generate the harmonic mechanical excitation. The flywheels are rotated by motor 41 and driving cog wheels 42, 44. The frequency of the vibration can be varied and is related to the speed of the motor. While the vibrator and transducer probe are shown commonly housed in the exemplary embodiment of FIG. 2, it is contemplated that the vibrator 26 may be mounted onto the transducer probe or housed within a separate probe from that of the transducer elements. Additionally, it is contemplated that more than a pair of flywheels may be used to induce vibrations.

Figure 3:
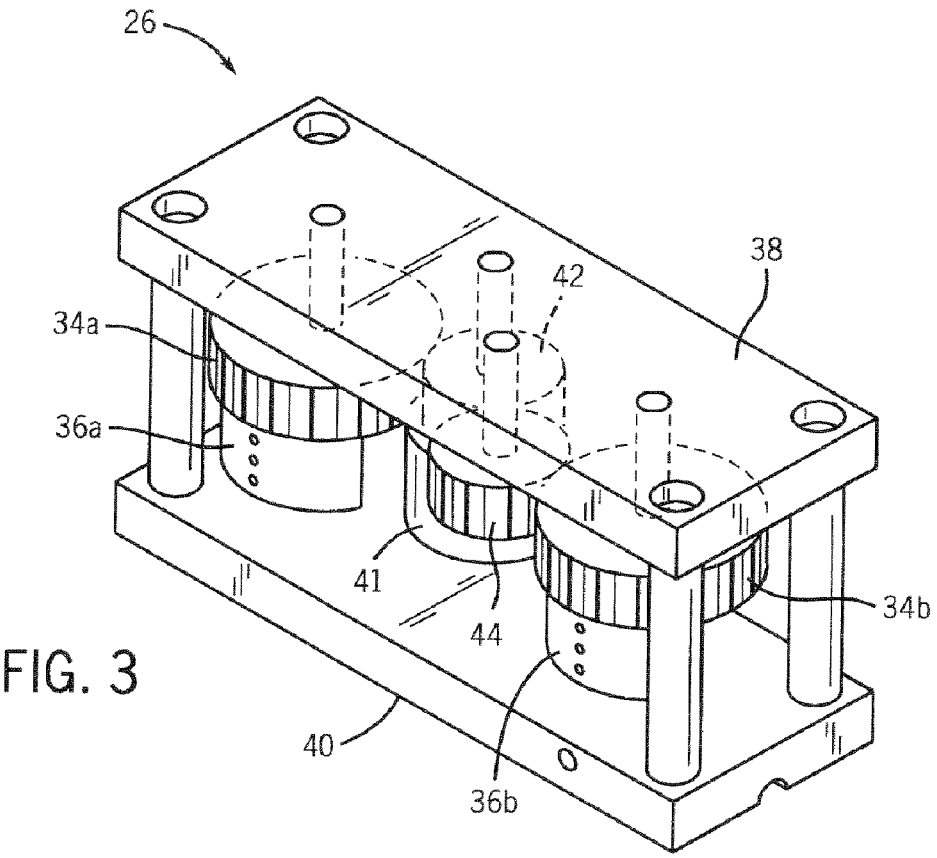
FIG. 3 is a perspective view of a vibrator according to the present invention.

Referring now to FIG. 3, a vibrator 26 according to the present invention is shown in perspective. As illustrated, vibrator 26 includes a pair of support plates 38, 40 having a pair of cog wheels 34(a), 34(b) and fly wheels 36(a), 36(b) supported therebetween. Disposed between the pair of cog wheels 34(a), 34(b) is a DC motor 41. The DC motor is connected to a motor cog wheel 42 that directly drives cog wheel 34(a) and indirectly drives cog wheel 34(b) via linking cog wheel 44. In this regard, the DC motor directly drives cog wheel 34(a) but indirectly drives cog wheel 34(b).

Cog wheels 34(a), 34(b) each support a fly wheel 36(a), 36(b), respectfully, that is driven based on the voltage applied to the DC motor. As will be described below, the centrifugal forces resulting from rotation of the flywheels causes the harmonic mechanical excitation described above along a principal axis. In this regard, the pair of flywheels are caused to rotate opposite one another. That is, one cog wheel and its associated flywheel rotates in a clockwise direction whereas the other cog wheel and its associated flywheel rotates in a counterclockwise direction. The cog wheels are connected such that the flywheels, when rotated, rotate at the same speed.

Preferably, the flywheels are small in weight, e.g., on the order of a few grams, and thus, the entire vibrator can be housed within a handheld probe. Moreover, as a result of the relatively reduced size of the vibrator, it has little impact on the magnetic and RF fields generated during magnetic resonance imaging. As referenced above, the vibrator may be mounted to or integrated with the ultrasound transducer of an ultrasound system. In this regard, the sonographer may perform the ultrasound with a freehand examination thereby eliminating the need for the sonographer to use one hand to control the ultrasound transducer and the other hand to manipulate the vibrator. One skilled in the art will appreciate that the frequency of the harmonic motion induced by the vibrator can be varied by changing the voltage applied to the DC motor. In a preferred embodiment, the mover drives the flywheels to provide harmonic motion between 1-600 Hz, so that the frequency dependence of elastic properties can be examined, as well.

Figure 4:
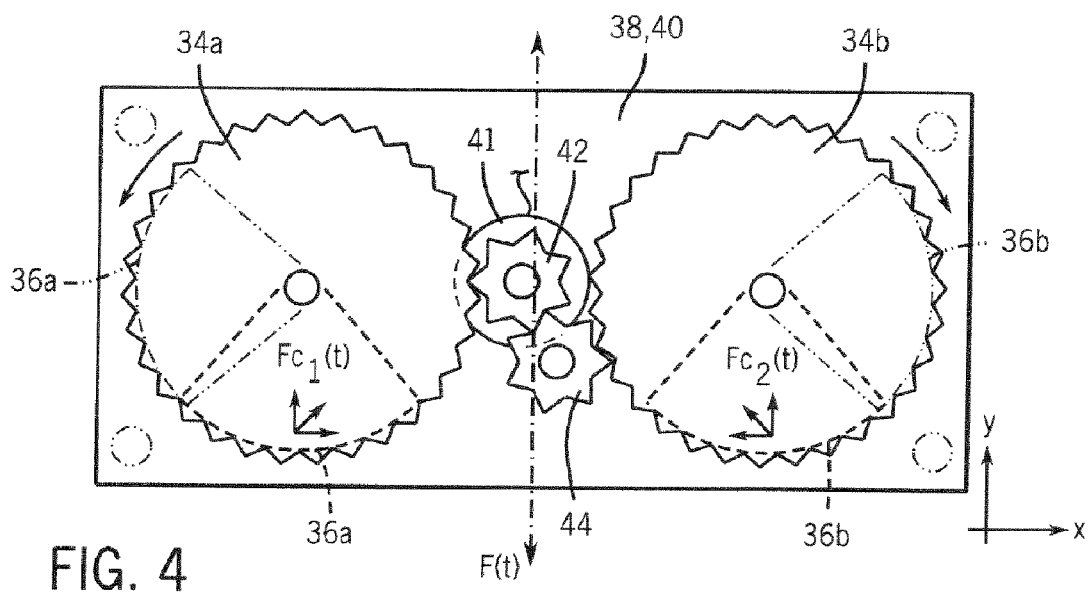
FIG. 4 is a schematic representation of the vibrator illustrated in FIG. 3.

Referring now to FIG. 4, the principle of operation of the vibrator 36 is schematically illustrated. As shown, the flywheels rotate opposite to one another. In this regard, one flywheel 36(a) rotates in a counterclockwise direction while flywheel 36(b) rotates in a clockwise rotation. Both flywheels preferably rotate at the same speed. By this arrangement as well as rotation of the fly wheels at a similar speed, the vibrational force schematically illustrated by F(t) that results from the centripetal forces $F_{C1}(t)$ and $F_{C2}(t)$ shows in one direction. The resulting force F(t) will accelerate the plates 38, 40 where the flywheels are connected so that the plate will perform a harmonic motion in the direction of F(t). Moreover, the clockwise and counterclockwise rotation of the flywheels at the same speed cancels out any vibratory forces in the x-direction thereby resulting in vibration only in the y-direction.

Therefore, an imaging tool to introduce a vibrational force into an object is disclosed. The imaging tool includes a housing and at least a pair of flywheels disposed in the housing. The imaging tool further has a motor disposed in the housing and operably connected to the pair of flywheels to cause rotation of the flywheels to introduce a harmonic mechanical excitation to an object placed in proximity to the housing.

An ultrasound transducer probe is also presented and includes a probe housing as well as an array of piezoelectric transducer elements disposed within the housing that when energized cause transmission of ultrasonic sound waves to an object to be imaged. The transducer elements are also constructed to be impinged by ultrasonic sound waves and in response thereto emit electrical current that can be processed to reconstruct an image of the object. The transducer probe further includes a mechanical vibrator that causes harmonic excitation of tissue within the object during imaging of the object.

The present invention is also directed to an ultrasound system having a CPU that coordinates data collection and image reconstruction for an ultrasound scan. The system further has a display connected to the CPU that displays an image reconstructed from acquired ultrasound data processed by the CPU. A transducer probe is connected to the CPU and sends and receives sound waves for the acquisition of ultrasound data. The ultrasound system further has a vibrator connected to the CPU that causes harmonic excitation within an object to be imaged in the ultrasound scan.

The present invention has been described in terms of the preferred embodiment, and it is recognized that equivalents, alternatives, and modifications, aside from those expressly stated, are possible and within the scope of the appending claims.

What is claimed is:

1. An ultrasound transducer probe comprising:
a transducer probe housing;
an array of piezoelectric transducer elements disposed within the housing that when energized cause transmission of ultrasonic sound waves to an object to be imaged and when impinged by ultrasonic sound waves emit electrical currents that can be processed to reconstruct an image; and
a mechanical vibrator comprising a pair of flywheels of a same size, wherein one flywheel rotates in one rotational direction, wherein the other flywheel rotates in an opposite rotational direction at a same time and at a same speed, thereby causing harmonic excitation of tissue within the object during imaging of the object, further wherein the harmonic excitation of tissue is only along a single axis.

2. The probe of claim 1 wherein the mechanical vibrator further comprises a pair of cog wheels, each of which supports a flywheel.

3. An ultrasound system comprising:
 a CPU that coordinates data collection and image reconstruction for an ultrasound scan;
 a display connected to the CPU that displays an image reconstructed from acquired ultrasound data processed by the CPU;
 a transducer probe connected to the CPU that sends and receives sound waves for the acquisition of ultrasound data; and
  a vibrator connected to the CPU that causes a harmonic excitation only in a single direction within an object to be imaged in the ultrasound scan, wherein the vibrator comprises:
   a pair of flywheels of a same size, wherein one flywheel rotates in one rotational direction, wherein the other flywheel rotates in an opposite rotational direction at a same time and at a same speed, thereby causing the harmonic excitation;
   a pair of cogwheels, each of which supports a flywheel; and
   a DC motor that causes rotation of the pair of cog wheels.

4. The system of claim 3 wherein the transducer probe is mounted to the vibrator, and wherein the CPU causes the vibrator to cause harmonic excitation as soon as the transducer probe begins transmission of sound waves.

5. The system of claim 3 wherein the CPU controls voltage applied to the DC motor to control harmonic excitation frequency.

6. The system of claim 3 wherein the CPU is configured to acquire ultrasound data for elastrographic images.

7. The system of claim 3 wherein the vibrator causes harmonic excitation in the object in a range of 1-600 Hz.

* * * * *